US005981267A

United States Patent [19]
Wong et al.

[11] Patent Number: 5,981,267
[45] Date of Patent: *Nov. 9, 1999

[54] ENANTIOSELECTION OF AMINES USING HOMOCARBONATES WITH HYDROLASE

[75] Inventors: Chi-Huey Wong, Rancho Santa Fe, Calif.; Bernard Orsat, Allschwil, Switzerland; Wilna J. Moree; Shu Takayama, both of San Diego, Calif.

[73] Assignee: The Scripps Research Institute, La Jolla, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/590,530

[22] Filed: Jan. 24, 1996

[51] Int. Cl.[6] .................................................... C07C 1/04
[52] U.S. Cl. ............................................. 435/280; 435/128
[58] Field of Search ...................................... 435/280, 128

[56] References Cited

U.S. PATENT DOCUMENTS 5,002,880   3/1991   Mason ....................................... 435/128

FOREIGN PATENT DOCUMENTS 310012   4/1989   European Pat. Off. .

OTHER PUBLICATIONS

Boland et al., "Esterolytic and Lipolytic Enzymes in Organic Synthesis", Synthesis, Dec. 1991: 1049–72.

Whitesides G. et al., "Enzymes as Catalysts in Synthetic Organic Chemistry", Angwandte Chemie 24(8): 617–718 (1985).

Orsini F. et al., "Study of the Resolution of Amino Acids and amino alcohols in organic Soluents", Amino Acids 9: 135–140 (1995).

Petrova D. et al., "Reduction of same 2—thiazoline benzamide and carbanate derivatives with LiAlhy", Croat. Chem. Acta. 40:189–94 (1968).

Wang et al., "Lipase–Catalyzed Irreversible Transesterifications Using Enol Esters as Acylating Reagents: Preparative Enantio–and Regioselective Syntheses of Alcohols, Glycerol Derivati es, Sugars and Organometallics" J. Am. Chem. Soc. 110:7200–7205 (1988).

Fernandez, et al., "Lipase–catalysed Enantioselective Acylation of N–Protected or Unprotected 2–Aminoalkan–1–ols", *J. Chem. Soc., Perkin Trans.*, 1:2885–2889 (1992).

Gotor, et al., "Synthesis of Optically Active Amides from β–Furyl and β–Phenyl Esters by way of Enzymatic Aminolysis", *J. Chem. Soc., Perkin Trans.*, 1:2453–242456 (1993).

Kitaguchi, et al., "Enzymatic Resolution of Racemic Amines: Crucial Role of the Solvent", *J. Am. Chem. Soc.*, 111:3094–3095 (1989).

Pozo, et al., "Vinyl Carbonates as Novel Alkoxycarbonylation Reagents in Enzymatic Synthesis of Carbonates", *Tetrahedron*, 48(31):6477–6484 (1992).

Pozo and Gotor, Kinetic Resolution of Vinyl Carbonates through a Lipase–Mediated Synthesis of their Carbonate and Carbonate Derivatives, *Tetrahedron*, 49(46):10725–10732 (1993).

*Primary Examiner*—Sandra E. Saucier
*Attorney, Agent, or Firm*—Donald G. Lewis

[57] ABSTRACT

Racemic amines are enzymically converted by enantioselective carbamation to produce to chiral carbamates. Simple homocarbonates employed as substrates. The chiral carbamates may then be deprotected to yield the original amine in a chiral form. Alternatively, the chiral carbamates may be reduced so as to produce methylated chiral amines.

23 Claims, 7 Drawing Sheets

(R = methyl, ethyl, allyl)

(R = methyl, ethyl, allyl)

ENANTIOSELECTION OF AMINES USING HOMOCARBONATES WITH HYDROLASE

FIELD OF THE INVENTION

The invention relates to enantioselective acylations of amines and to the enantioselective resolution of amines. More particularly, the invention relates to the enantioselective acylation and resolution of amines using esterases and homocarbonate substrates to form chiral carbamates.

BACKGROUND

Racemic amines may be enantiomerically resolved using various physico-chemical separation techniques after derivation with a tag molecule. M. Pawlowska et al. disclose a method for enantiomerically separating aliphatic and aromatic amines using aromatic anhydrides as nonchiral derivatizing agents. (*Journal of Chromatography A*. (1994): vol. 666(1-2):485–91.) Alternatively, T. Toyo'oka et al. disclose a method for enantiomerically separating amines using chiral tagging reagents and high-performance liquid chromatography. (*Biomedical Chromatography* (1994): vol. 8(2): 85–9.)

Racemic amines may also be enantiomerically resolved without tagging or derivation using various chiral physico-chemical separation techniques. N. Huynh et al. disclose a chromatographic separation of enantiomeric amines using N-benzyloxycarbonyl-glyclyl-L-proline as a counter ion in methanol. (*Journal of Chromatography A*. (1995): vol. 705 (2):275–87. S. Branch et al. disclose a separation method employing capillary electrophoresis with cyclodextrins for separating enantiomers of phenethylamine. (*Journal of Pharmaceutical & Biomedical Analysis* (1994): vol. 12(12): 1507–17. R. Kuhn et al. disclose the use of capillary zone electrophoresis with optically active crown ethers for separating enantiomers. (*Electrophoresis* (1994): vol. 15(6): 828–34.) J. Mazzeo et al. disclose the use of micellar electrokinetic capillary chromatography using novel chiral surfactants for separating enantiomers of amines. (*Journal of Chromatography A*. (1994): vol. 680(1):125–35.)

Amines may also be enantiomerically resolved by the enzymatic formation of amides using esters as substrates. (H. Kitaguchi, et al., *J. Am. Chem. Soc.*, (1989): vol. 111, pp 3094; S. Fernandez et al., *J. Chem. Soc. Chem. Commun.* (1992): pp 2885; and V. Gotor, et al., *J. Chem. Soc. Chem. Commun.* (1993): pp 2453.) These unsymmetrical carbonates are, however, not readily available and may be too reactive to avoid non-enzymatic reactions. Methods for protecting amines by derivation with vinyl carbonates using the lipase from Candida antarctica have been reported. (M. Pozo, et al., *Tetrahedron* (1992): vol. 48, pp 6477; M. Pozo et al., *Tetrahedron* (1993): vol. 49, pp 10725.)

Unlike the enantiomeric resolution of amines, methods for the enantiomeric resolution of alcohols are relatively well developed. Racemic alcohols may be resolved by an irreversible enzymatic acylation using lipases or serine proteases as catalysts in high concentrations of organic solvents. Preferred acylation reagents include activated esters such as trifluoroethyl-, choloroethyl-, cyanomethyl-, enol-, oxime- or thioesters, or anhydrides. Methods for enzymatically acylating alcohols have been extensively reviewed. (Klibanov. A., *Acc. Chem. Res.* (1990): vol. 23, pp 114; Wong, C.-H. et al., *Enzymes in Synthetic Organic Chemistry*, Pergamon, Oxford, 1994, pp 72; and J.-M. Fang, J.-M et al., *Synlett*. (1994): vol. 6, pp. 393.) Enol esters are preferred acylating reagents for alcohols. (See: H. M. Sweers et al., *J. Am. Chem. Soc.* (1986): vol. 108, pp 6421; M. Degueil-Castaing, et al., *Tetrahedron Lett.* (1987): vol. 28, pp 953; Y. Wang, et al., *J. Am. Chem. Soc.* (1988): vol. 110, pp 7200; and K. Laumen, et al., *J. Chem. Soc., Chem. Commun.* (1988), pp 1459.) The rate of enzymatic acylation for enol esters is relatively fast. Furthermore, since the released enol is spontaneously tautomerized to a ketone, the process irreversible and free of any inhibition that might be caused by the leaving alcohol. The product is easy to isolate. These acylating reagents, however, can not be used in the enzymatic acylation of amines as they are too reactive and give high background reactions.

What is needed is a method for enantiomerically resolving amines by an enzymatic derivation with homocarbonates to form chiral carbamates.

SUMMARY

Carbamates are obtained enantioselectively by enzymatic alkoxycarbonylation using homocarbonates as substrates. Depending on the solubility of the amine substrate, the reaction can be carried out in organic or aqueous medium. This new versatile irreversible process was used in the enantioselective protection of aziridine, α-aminoalcohol, β-aminoester and diaminocyclitol using Candida cylindracea lipase or Subtilisin BPN' as catalyst. Of several homocarbonates investigated, diallyl carbonate is the best. The carbamate product can be easily deprotected or converted to the N-methyl derivative by reaction with $LiAlH_4$, providing a new process for the enantioselective chemoenzymatic methylation of amine-containing compounds.

The enzymatic process employs commercially available, low cost homocarbonates for the protection of amines with high chemo- and enantioselectivity. Diallyl carbonate is shown to be the most useful substrate for the reaction, providing the highest yield and enantioselectivity. This process can be carried out in aqueous (for primary and secondary amines) or organic solutions (for secondary amines). The process can be scaled up and a broad array of alterative substrates may be employed. some of these reactions and to find new substrates.

One aspect of the invention is directed to a method for enantioselectively acylating an amine for producing a chiral carbamate. The method employs the step of enzymatically acylating the amine with a homocarbonate for producing the chiral carbamate. Preferred homocarbonate include dimethyl carbonate, diethyl carbonate, and diallyl carbonate. Preferred enzymes for catalyzing the enzymatic acylation include Candida cylindracea lipase and Subtilisin BPN'. Preferred amines include primary and secondary amines, and more particularly include aziridine, α-aminoalcohol, β-aminoester, and diaminocyclitol.

Another aspect of the invention is directed to a method for separating a first enantiomer of an amine from a second enantiomer of the amine. A preferred mode of this aspect of the invention includes three steps. Firstly, the first enantiomer of the amine is enzymatically acylated with a homocarbonate to form a chiral carbamate. Then, the chiral carbamate is separated from the second enantiomer of the amine. And finally, the chiral carbamate is deprotected to obtain the first enantiomer of the amine, separate from the second enantiomer of the amine. Preferred homocarbonates include dimethyl carbonate, diethyl carbonate, and diallyl carbonate. Preferred enzymes for catalyzing the acylation of the first enantiomer of the amine include Candida cylindracea lipase and Subtilisin BPN'. In a preferred mode, the chiral carbamate is separated chromatographically from the second enantiomer of the amine and the chiral carbamate is deprotected by hydrolysis. Preferred amines include primary and secondary amines and, more particularly, include aziridine, α-aminoalcohol, β-aminoester, and diaminocyclitol.

Another aspect of the invention is directed to a method for enantioselectively methylating an amine. A preferred mode of this aspect of the invention includes three steps. Firstly, one enantiomer the amine is enzymatically acylated of with a homocarbonate for producing a chiral carbamate. Then, the chiral carbamate is separated from unreacted amine. And finally, the chiral carbamate is reduced to obtain a chiral N-methyl amine. In a preferred mode, the chiral carbamate is reduced with $LiAlH_4$. Preferred homocarbonates include dimethyl carbonate, diethyl carbonate, and diallyl carbonate. Preferred enzymes for catalyzing the acylation include *Candida cylindracea* lipase and Subtilisin BPN'. In preferred mode, the chiral carbamate of said Step A is separated chromatographically from unreacted amine. Preferred amines include primary and secondary amines and, more particularly, aziridine, α-aminoalcohol, β-aminoester, and diaminocyclitol.

Another aspect of the invention is directed to a method for converting an α-hydroxylamine wherein a α-carbon is racemic to an α-hydroxyamide wherein the α-carbon is chiral. A preferred mode of this aspect of the invention includes two steps. Firstly, the α-hydroxylamine is enzymatically bisacetylated with vinyl acetate for producing an α-acetoxyamide wherein the α-carbon is chiral. Then, the α-carbon of the α-acetoxyamide is enzymatically hydrolyzed for producing the α-hydroxyamide wherein the α-carbon is chiral. A preferred enzyme for catalyzing the enzymatic bisacetylation is Subtilisin BPN'. A preferred enzyme for catalyzing the hydrolysis is PS-800.

Another aspect of the invention is directed to a method for enantioselectively converting an α-hydroxycarbamate to an α-acetoxycarbamate. In a preferred mode of this aspect of the invention, the α-hydroxycarbamate is enzymatically acetylated for producing the α-acetoxycarbamate using vinyl acetate as a substrate. Preferred enzymes for catalyzing the acetylation include PS-30 and *Candida cylindracea* lipase.

BRIEF DESCRIPTION OF DRAWINGS

FIG. 2 illustrates an experiment in which a racemic aziridine 1 was stirred at ambient temperature with diallyl carbonate in phosphate buffer (pH 8.0), containing Subtilisin BPN'. Carbamate 4 was obtained in 50% yield after 2 h. Both dimethyl- and diethyl carbonates reacted more slowly; after 90 hours, 2 and 3 were obtained in 15 and 24% yield respectively. Disappointingly, the enantiomeric excess (ee) of each product determined by HPLC using a chiral column (Chiralcel OD-H, Daicel) was less than 25%. Adding 75% of 1,4-dioxane to the diallyl carbonate system gave a maximum yield of 39% after 74 hours and 54% ee. Switching from Subtilisin BPN' to *Candida cylindracea* lipase (CCL), also called *Candida rugosa* (CRL), and using the carbonates as solvents at rt for 45 hours gave better results. Due to its crystalline nature, dibenzyl carbonate could not be used in this procedure. Typical conditions use 1 mL homocarbonate, 20 mg CCL (*Candida cylidracea*) at room temperature for 40 hours (0.1 mmol of 1 per milliliter of homocarbonate was used).

DETAILED DESCRIPTION

Figure 1:
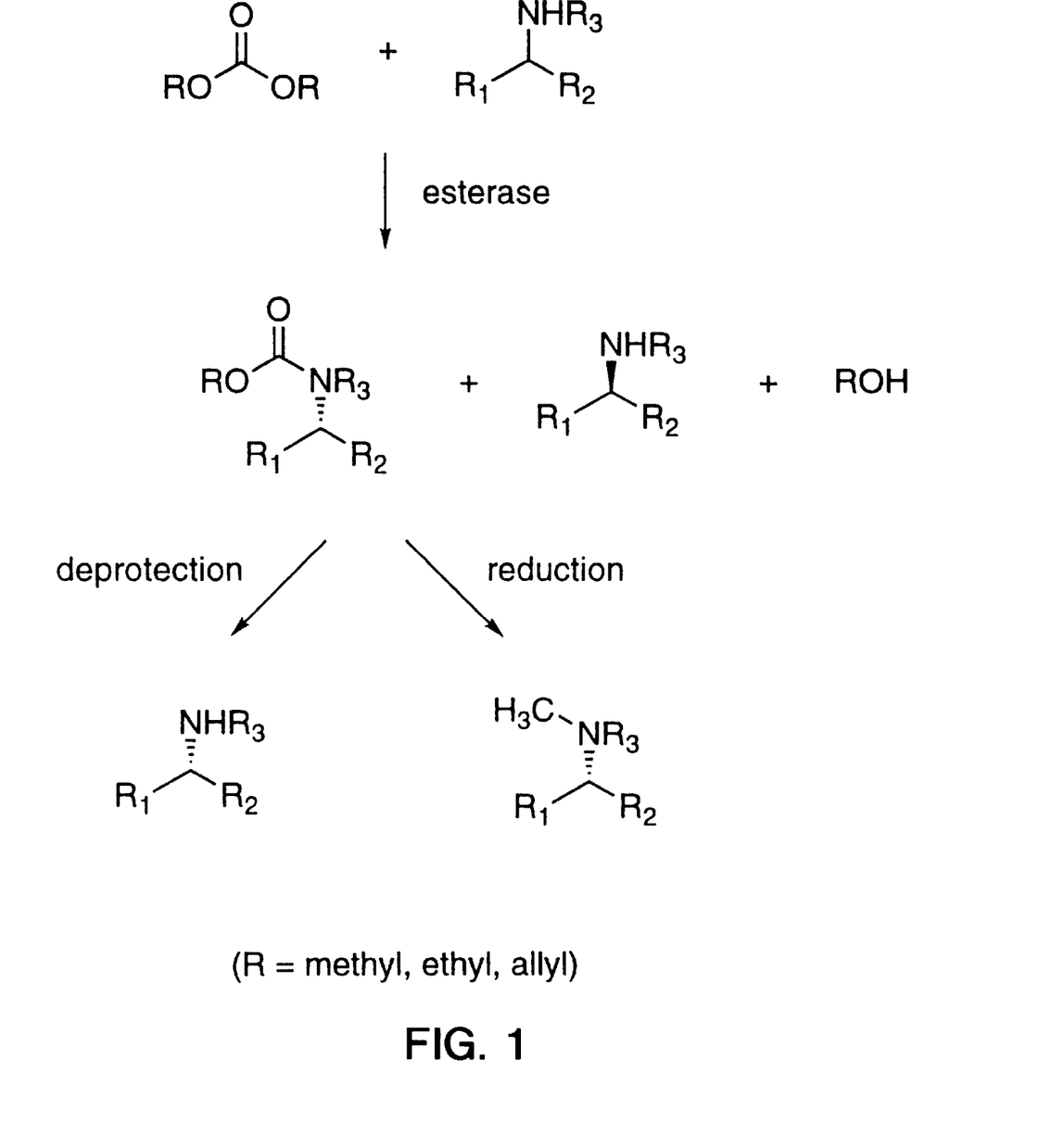
FIG. 1 illustrates a novel enzymatic method for protecting amines as carbamates with high enantioselectivity using commercially available and low cost homocarbonates as substrates for lipases and proteases. The reactions are irreversible as the product carbamates are not substrates for the serine-type esterases. The carbamate can be easily deprotected or converted to the N-methyl derivative by reaction with $LiAlH_4$, providing a new procedure for the chemoenzymatic methylation of amines.
Figure 2:
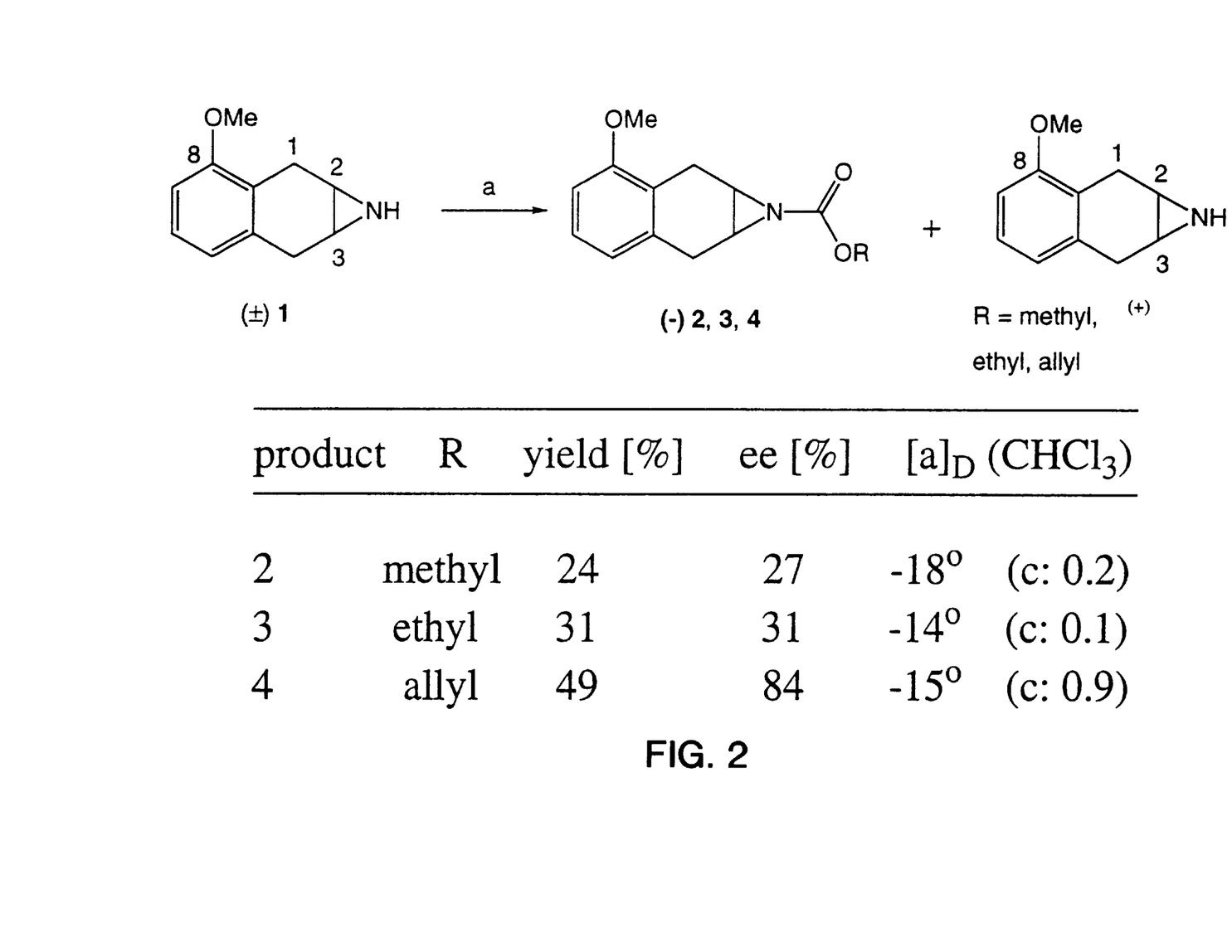

As illustrated in FIG. 2, amines are protected as carbamates with high enantioselectivity using commercially available and low cost homocarbonates as substrates for lipases and proteases. The reactions are irreversible as the carbamate products are not substrates for the serine-type esterases. Furthermore, the symmetrical structure of the homocarbonates gives unambiguously a single carbamate product, making the process very simple. The carbamate can be easily deprotected or converted to the N-methyl derivative by reaction with $LiAlH_4$, providing a facile procedure for the chemoenzymatic methylation of amines.

EXAMPLE 1

As illustrated in FIG. 2, racemic aziridine 1 was stirred at ambient temperature with diallyl carbonate in phosphate buffer (pH 8.0), containing Subtilisin BPN'. Carbamate 4 was obtained in 50% yield after 2 hours. Both dimethyl- and diethyl carbonates reacted more slowly; after 90 hours, 2 and 3 were obtained in 15 and 24% yield respectively. An identical reaction without enzyme did not provide any detectable product over the same period. The enantiomeric excess (ee) of each product determined by HPLC using chiral column (Chiralcel OD-H, Daicel) was less than 25%. Adding 75% of 1,4-dioxane to the diallyl carbonate system gave a maximum yield of 39% after 74 hours and 54% ee. Once again, an identical reaction without enzyme did not provide any detectable product over the same period.

Switching from Subtilisin BPN' to *Candida cylindracea* lipase (CCL), also called *Candida rugosa* (CRL), and using the carbonates as solvents at room temperature for 45 hours gave better results. Due to its crystalline nature, dibenzyl carbonate could not be used in this procedure. Racemic 4 was also prepared by a standard procedure and used as a reference for spectroscopic and chromatographic analyses. (G. Sennyey, et al., *Tetrahedron Lett.* (1987): vol. 28, p 5809.)

EXAMPLE 2

Figure 3A:
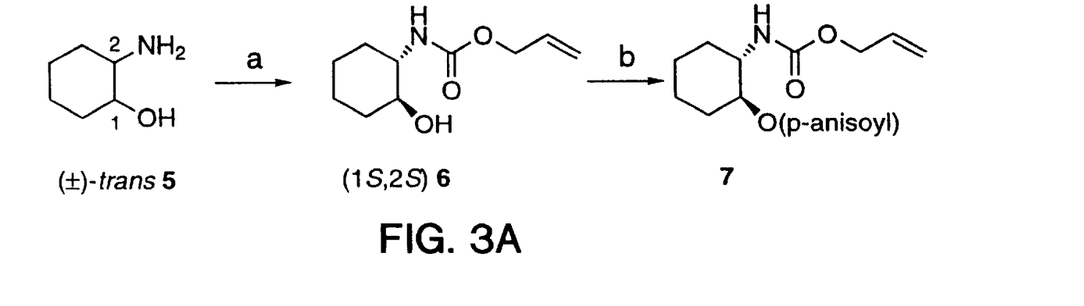
FIG. 3 illustrates enzymatic resolution/protection of primary amines with diallyl carbonate in aqueous buffer and subtilisin BPN'. Conditions are as follows: (a) Diallyl carbonate (0.6 mmol, 3 eq), phosphate buffer (0.1 M, pH 8.0, 1 mL), BPN' (10 mg), rt, 69 hours, 49% yield, 78% ee. (b) p-anisoyl chloride (1.1 eq), pyridine (2 eq), DMAP (4-dimethylaminopyridine, 0.1 eq), methylene chloride (0.10 Molar), rt, 24 h. © Diallyl carbonate (0.2 mmol, 3.3 eq), phosphate buffer (0.1 M, pH 8.0, 1 mL), BPN' (6 mg), rt, 85 hours, 45% yield, 93% ee. d) Diallyl carbonate (1.23 mmol, 4 eq×4), HEPES buffer (0.2 M HEPES, 0.02 M $CaCl2$, pH 7.8, 3 mL), DMF (3 mL), BPN' (10 mg), rt, 1 week, 76% yield, >99% ee.
Figure 3B:
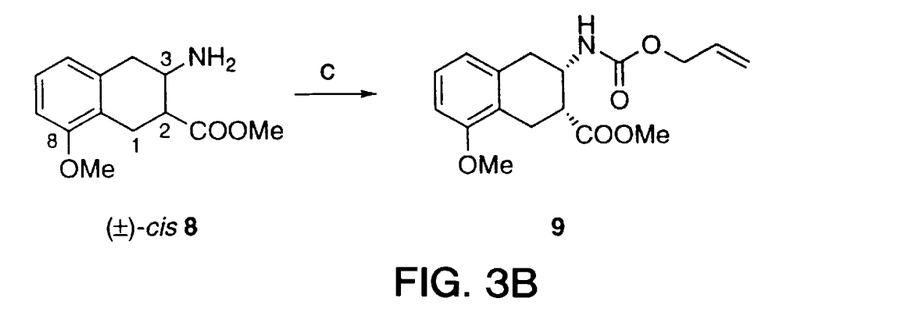
Figure 3C:
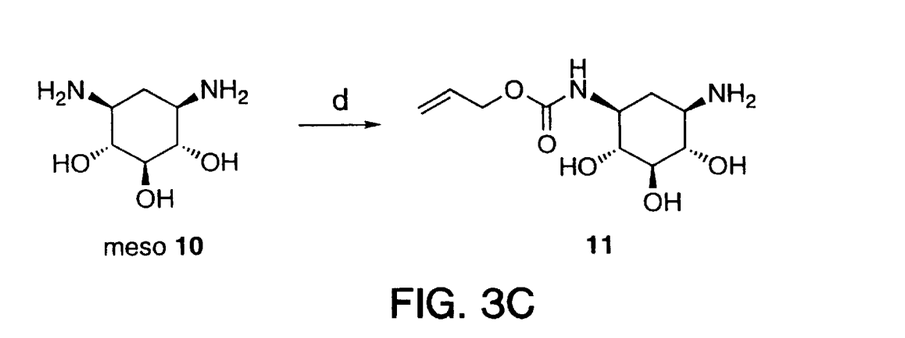

As illustrated in FIG. 3, when primary amines were mixed with diallyl carbonate as solvent, a significant background reaction was observed without enzyme. In aqueous buffer, however, no background reaction was detected and the use of Subtilisin BPN' appeared to be useful for the enzymatic protection of amines under these conditions. Three multifunctional substrates which could undergo different enzymatic reactions were then characterized in order to elucidate the chemo- and enantioselectivity of this process. When racemic 5 was used as substrate, the reaction was carried out in phosphate buffer (pH 8.0) with Subtilisin BPN' and diallyl carbonate (Scheme III). After 69 hours, 6 was obtained in 49% yield and 78% ee determined by HPLC (Chiralpak AD, Daicel), based on the O-(p-anisoyl) derivative 7 (Scheme III). Carbamate 6 was subsequently deprotected according to a conventional procedure to provide 5 after enzymatic resolution. (H. Kunz, et al., *Angew. Chem., Int. Ed. Engl.* (1984): vol. 23, pp 436.) The optical rotation of the obtained 5 ($[\alpha]_D$+140°, c 0.8, $H_2O$) was then compared with the published value to establish the absolute configuration (1S, 2S) for the enzyme product. (K. Faber et al., *Tetrahedron Lett.* (1988): vol, 29, pp 1903.) When dibenzyl carbonate was used instead of diallyl carbonate, only a trace of product was observed. This carbonate remained present in the reaction mixture, indicating that it is a poor substrate for the enzyme. Racemic β-aminoester 8, was treated similarly for 85 hours and carbamate 9 was obtained with 93% ee determined by HPLC (Chiralpak AD, Daicel) and in 45% yield without hydrolysis of the ester. When the concentration of 8 was increased to 0.1 M in the presence of 11 mg/mL of Subtilisin, 9 was obtained in 40% yield. At 0.3 M concentration of the substrate, 9 was obtained in 35% yield using 31 mg/mL of Subtilisin. The meso substrate 2-deoxystreptamine, 10, was converted to 11 through the use of subtilisin BPN' and diallyl carbonate in HEPES buffer (200 mM, pH 7.8, 20 mM $CaCl_2$, 50% DMF). The chemo- and enantioselectivity of the reaction was complete despite 5 possible sites of reaction. The product was obtained in 76% yield and >99% ee determined by HPLC (Chiralpak AD, Daicel), based on the peracetylated p-toluenesulfonamide derivative.

EXAMPLE 3

Figure 4:
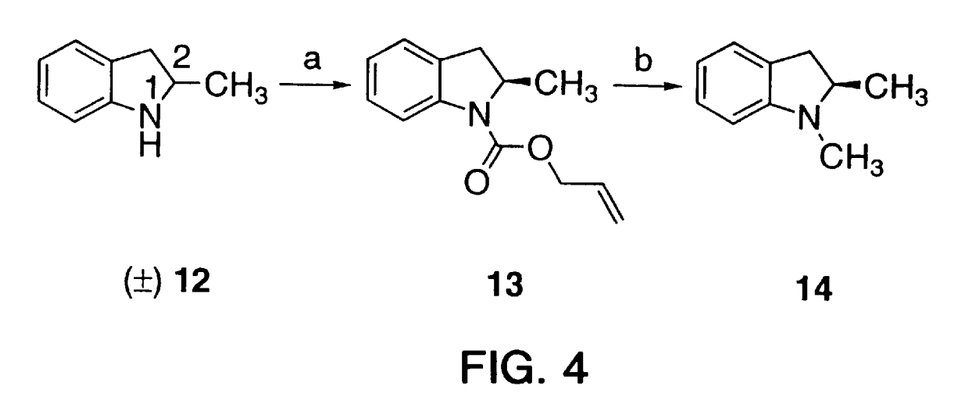
FIG. 4 illustrates the resolution of racemic secondary amine 12 with diallyl carbonate in aqueous buffer and subtilisin BPN'. Conditions are as follows: a) Diallyl carbonate (1.5 mmol, 1.5 eq), phosphate buffer (0.1 M, pH 8.0, 10 mL), BPN' (50 mg), rt, 92 hours, 6% yield, 93% ee. (b) $LiAlH_4$ (8.7 eq), ether, 0° C., 2 hours, 93%.

As illustrated in FIG. 4, the process was also applied to the resolution of racemic secondary amine 12. The enzymatic reaction was carried out for 92 hours to yield 13 with 93% ee determined by HPLC (Chiralcel OD-H, Daicel) and in 6% yield. The low yield was attributed to the stearic hindrance and unfavorable electronic effects occurring at the reacting center. The reaction was also attempted using diallyl carbonate as solvent and *Candida cylindracea* lipase as catalyst, but no reaction was observed. The carbamate was subsequently reduced to the N-methyl derivative using $LiAlH_4$ in ether to afford 14 in 93% yield. Resolution of racemic amino acids can also be carried out similarly with diallyl carbonate. Both phenylalanine and alanine were converted to the carbamates in ~40% yield and >90% ee.

EXAMPLE 4

Figure 5:
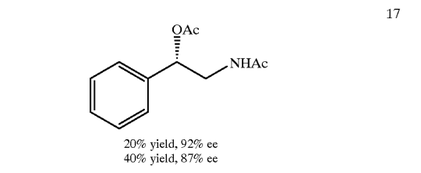
FIG. 5 illustrates enzymatic resolution/protection of 2-amino-1-phenylethanol and related derivatives using various substrates including diallyl carbonate, vinylacetate, diisopropyl ether (hydrolysis reaction) or vinylbutyrate in aqueous buffer. The enzymes included subtilisin BPN', *Candida cylindracea* lipase (CCL), *Pseudomonas cepacia* (PS-30) or (PS-800). Reaction conditions are indicated for each scheme shown.
Figure 5A:
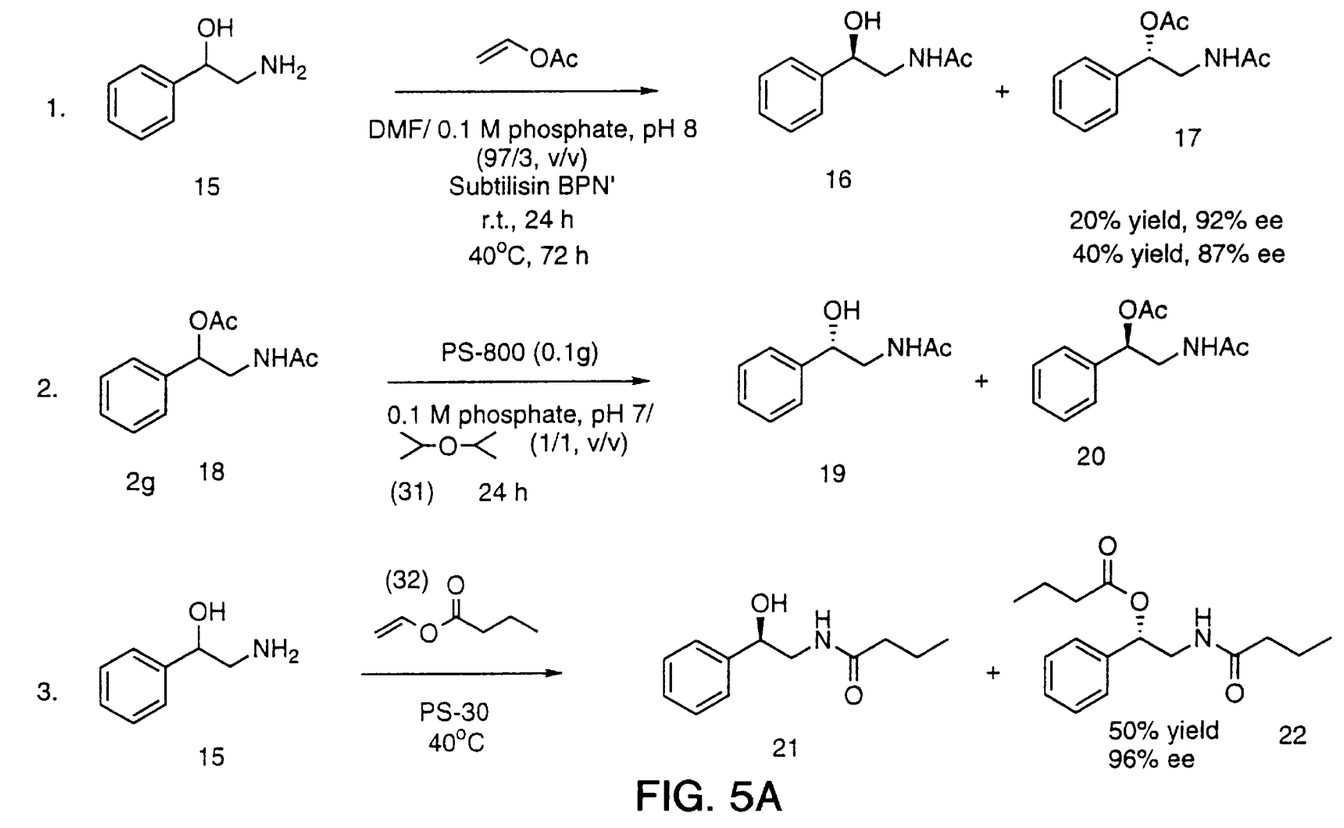
Figure 5B:
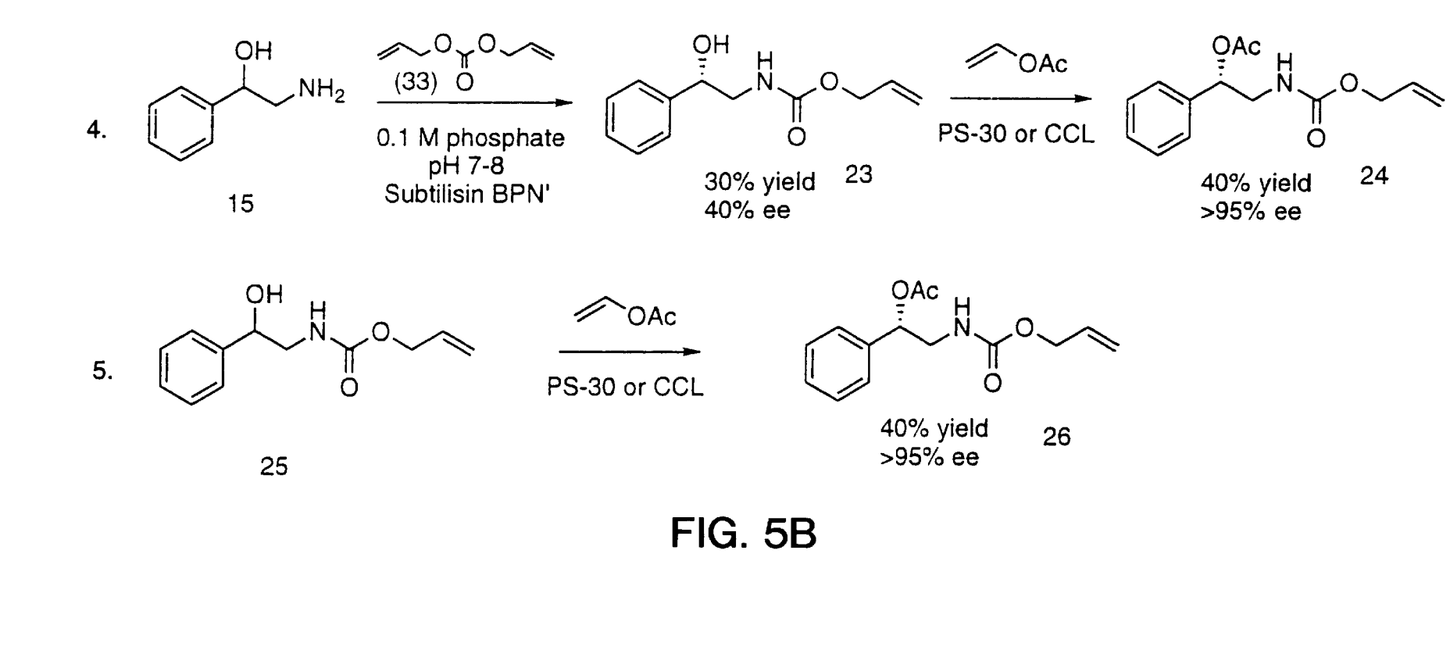

As illustrated in FIG. 5, when racemic mixtures of amino-alcohol compounds were exposed to vinylacetate and subtilisin BPN' or lipase from *Candida cylindracea*, a one pot resolution was achieved to generate a separable mixture of bisacetylated-acetamide-acetate and acetamide-alcohol products. The addition of excess vinylacetate to a DMF/pH 7 phosphate buffer solution with amino-alcohol compound 15, uncatalytically acylated the free amine moiety to form a racemic mixture of acetamide-alcohol in situ. The mixture of acetamide-alcohol was then concomitantly and enzymatically resolved in the same pot to afford a separable mixture of bisacetylated-acetamide-acetate 17 (40% yield; 87% ee) and acetamide-alcohol 16 (20% yield, 92% ee) via addition of subtilisin BPN' in the presence of excess vinylacetate for approximately 72 hours at 40° C.

It is also disclosed that a racemic mixture of acetamide-acetate compound 18 can be enzymatically resolved via hydrolysis of the acetamide-acetate to form a separable mixture of bisacetylated-acetamide-acetate 20 (50% yield; >99% ee) and recovered acetamide-alcohol 19 (50% yield). The procedure involves addition of 1.1 equivalents triethylamine, 1.0 equivalents acetic anhydride and 0.10 Molar methylene chloride to the corresponding acetamide-acetate, followed by purification and resuspension in a 1:1 v/v mixture of 0.1 M pH 7 phosphate buffer/diisopropyl ether (31) and lipase PS-800 for approximately 24 hours at 40° C. to afford the hydrolyzed 19 and unhydrolyzed bisacetylated-acetamide-acetate 20 in >99% enantiomeric excess.

Synthetic Protocals

General. Solvents and reagents used were purchased from Aldrich Chemical Co. and Fisher Scientific, with the exception that dibenzyl carbonate was purchased from Lancaster Synthesis Inc. *Candida cylindracea* lipase (CCL, type VII, 860 units/mg, L1754, EC 3.1.1.3) and Subtilisin BPN' (Nagarse, type XXVII, 8.3 units/mg, P4789) were both purchased from Sigma and *Pseudomonas cepacia* (PS-30) and *Pseudomonas cepacia* (PS-800) were purchased from Amano. $^1H$ NMR spectra were recorded on a Bruker AMX 400 (400 MHz) spectrometer and chemical shifts are given in ppm (δ) relative to TMS as internal standard. $^{13}C$ NMR spectra were measured with a Bruker AMX 400 (100 MHz) spectrometer and chemical shifts are given relative to $CDCl_3$ or MeOD as internal standard. Additionally, 250 MHz $^1H$-NMR and 100 MHz $^{13}C$-NMR were measured using a Bruker AC-250 spectrometer in $CDCl_3$ unless otherwise stated. High resolution mass spectra (HRMS) were obtained on a VG ZAB-ZSE Mass Spectrometer in fast atom bombardment. The ee's were determined using a Perkin-Elmer HPLC and chiral columns (Chiralcel OD-H, Chiralpak AD; Daicel) and optical rotations were obtained on a Rudolph Research Autopol III polarimeter. Thin layer chromatography analysis was perfomed on pre-coated Merck Silica gel (60 F-254) plates (0.25 mm). Spots were visualized with UV light, ninhydrin, $KMnO_4$ or AMC stain. Column chromatography was carried out on Merck Kieselgel 60 (230–400 Mesh, ASTM).

General Synthesis of Secondary Amine Compounds 2, 3 and 4 from Aziridine Compound 1 (FIG. 2):

2, 3, 4

Compounds (−) 2, 3, 4: Typically, 17.5 mg (0.1 mmol) of 1 (available from Sandoz pharmaceutical), 1 mL of carbonate and 20 mg of *Candida cylindracea* lipase were mixed and stirred at rt for 45 hours. $CH_2Cl_2$ was then added to the mixture, the enzyme filtered off and the filtrate concentrated in vacua. The product was isolated by silicagel preparative TLC (EtOAc/Hex 1:2) to afford solid compounds (−) 2, 3 or 4.

Deprotection Conditions to Form Free Amine:

N-Allyloxycarbonyl-compound 2, 3 or 4 (50 mg, 0.19 mmol) are deprotected according to the method of Boullanger et al. *Tetrahedron letters* 1986 27, 2599 (using $Pd(OAc)_2$ (2.2 mg, 0.01 mmol), $Et_3N$ (4.3 μL, 0.031 mmol), $Et_3SiH$ (triethylsilane) (47 μL, 0.29 mmol; commercially available from Aldrich) in $CH_2Cl_2$ (0.8 mL) employing a reaction time of 2 days. The amine is isolated in around 70% yield.

N-methyloxycarbonyl-1,4-dihydro-2,3-aziridine-8-methoxynaphthalene (2): yield: 24%. ee: 27%. $[\alpha]_D$−18° C. (c: 0.2, $CHCl_3$): $^1$H-NMR: δ 2.69 (br d, J=18.2 Hz, 1H), 3.01–3.02 (m, 2H), 3.06 (br d, J=17.6 Hz, 1H), 3.33 (br d, J=17.6 Hz, 1H), 3.61 (br d, J=18.2 Hz, 1H), 3.63 (s, 3H), 6.68 (m, 2H), 7.11 (t, J=7.9 Hz, 1H). HMRS for $C_{13}H_{16}O_3N$ (M+H), calcd 234.1130, found 234.1126.

N-ethyloxycarbonyl-1,4-dihydro-2,3-aziridine-8-methoxynaphthalene (3): yield: 31%. ee: 31%. $[\alpha]_D$−14° C. (c: 0.1, $CHCl_3$): $_1$H-NMR $^1$H-NMR: δ 1.20 (t, J=7.1 Hz, 3H), 2.69 (br d, J=18.1 Hz, 1H), 2.99–3.00 (m, 2H), 3.07 (br d, J=17.2 Hz, 1H), 3.34 (br d, J=17.2 Hz, 1H), 3.62 (br d, J=18.1 Hz, 1H), 3.80 (s, 3H), 4.04 (q, J=7.1 Hz, 2H), 6.68 (dd, J=3.4, 7.9 Hz, 2H), 7.10 (t, J=7.9 Hz, 1H). HMRS for $C_{14}H_{17}O_3NNa$ (M+Na): calcd, 270.1106; found, 270.1118.

N-allyloxycarbonyl-1,4-dihydro-2,3-aziridine-8-methoxynaphthalene (4): yield: 49%. ee: 84%. $[\alpha]_D$−15° C. (c: 0.9, $CHCl_3$): $^1$H-NMR $^1$H-NMR: δ 2.70 (br d, J=18.0 Hz, 1H), 2.99–3.04 (m, 2H), 3.08 (br d, J=17.0 Hz, 1H), 3.34 (br d, J=17.0 Hz, 1H), 3.62 (br d, J=18.0 Hz, 1H), 3.79 (s, 3H), 4.47 (br d, J=5.8 Hz, 2H), 5.20 (dd, J=1.2, 10.4 Hz, 1H), 5.28 (ddd, J=1.2, 2.9, 17.1 Hz, 1H), 5.78–5.93 (m, 1H), 6.65–6.70 (m, 2H), 7.11 (t, J=7.1 Hz, 1H). HMRS for $C_{15}H_{17}O_3NNa$ (M+Na): calcd, 282.1106; found, 282.1098.

Synthesis of Trans-N-allyloxycarbonyl-2-aminocyclohexanol (6) as illustrated in FIG. 3:

6

(1S, 2S)

Compound 6: 23 mg (0.2 mmol) 5 (free amine) and 44 mg (0.3 mmol) of diallyl carbonate were mixed. 1 mL of phosphate buffer (0.1 M, pH 8.0) and 10 mg of Subtilisin BPN' were added. The mixture was stirred at rt for 20 hours, then 44 mg (0.3 mmol) of diallyl carbonate were added and the mixture was stirred for another 49 hours. The mixture was extracted (EtOAc) and concentrated in vacuo to afford 19.4 mg (49%) of solid 6. $[\alpha]_D$+11° (c: 0.3, $CHCl_3$). $^1$H-NMR: δ, 1.14–1.40 (m, 4H), 1.68–1.75 (m, 2H), 1.98–2.06 (m, 2H), 2.98 (br s, 1H), 3.26–3.40 (m, 2H), 4.57 (d, J=5.6 Hz, 2H), 4.83 (br s, 1H), 5.22 (ddd, J=1.1, 2.5, 10.4 Hz, 1H), 5.31 (ddd, J=1.5, 3.0, 17.2 Hz, 1H), 5.91 (ddd, J=5.6, 10.4, 17.2 Hz, 1H). $^{13}$C-NMR: δ, 24.01, 24.60, 31.75, 34.10, 56.97, 65.85, 75.00, 117.91, 132.61, 157.19. HMRS for $C_{10}H_{18}O_3N$ (M+H): calcd, 200.1287; found, 200.1295.

Synthesis of Trans-N-allyloxycarbonyl-2-aminocyclohexyl methoxybenzoate (7) as illustrated in FIG. 3:

7

O-(p-anisoyl)

Compound 7: 19.4 mg (0.1 mmol) of 6 and 4 mL of $CH_2Cl_2$ were mixed. 20 μL of pyridine (0.24 mmol), 14 μL of p-anisoyl chloride (0.1 mmol) and DMAP (0.1 equivalents—4-dimethylaminopyridine) were added. The mixture was stirred at rt for 15 hours. 2 mL of a $NaHCO_3$ saturated solution were then added and the mixture was stirred at rt for 30 min. The solvent was then removed in vacuo, the residue extracted (Hexanes) and the product isolated by silicagel preparative TLC (EtOAc (ethylacetate)/Hex 1:10) to afford 27.2 mg (84%) of solid derivative 7. $^1$H-NMR: β, 1.30–1.64 (m, 4H), 1.74–1.82 (m, 2H), 2.11–2.16 (m, 2H), 3.78 (br d, J=9.6 Hz, 1H), 3.86 (s, 3H), 4.44 (d, J=4.7 Hz, 2H), 4.75–4.85 (m, 2H), 5.05 (br d, J=10.3 Hz, 1H), 5.15 (br d, J=17.5 Hz, 1H), 5.70–5.77 (m, 1H), 6.91 (d, J=8.8 Hz, 2H), 8.0 (d, J=8.8 Hz, 2H). $^{13}$C-NMR: δ, 24.04, 24.39, 31.17, 32.39, 54.29, 55.42, 65.30, 75.36, 113.52, 117.29, 122.54, 131.85, 132.82, 155.83, 163.42, 166.55. HMRS for $C_{18}H_{232}O_5NCs$ (M+Cs): calcd, 466.0631; found, 466.0645.

Synthesis of N-allyloxycarbonyl-1,4-dihydro-3-amino-8-methoxy-2-naphtoic acid methylester (9):

9

OMe

COOMe

Compound 9: 14 mg (0.06 mmol) of 8 (supplied from Sandoz pharmaceuticals) and 14 mg (0.1 mmol) of diallyl carbonate were mixed. 1 mL of phosphate buffer (0.1M, pH 8.0) and 6 mg of Subtilisin BPN' were added. The mixture was stirred at rt for 24 hours, then 14 mg (0.1 mmol) of diallyl carbonate were added and the stirring continued for another 61 hours. The mixture was extracted (EtOAc -ethylacetate), concentrated in vacuo. and the product isolated by silicagel preparative TLC (EtOAc/Hex 1:2) to afford 8.5 mg (45%) of solid 9. $[\alpha]_D$+26° (c: 0.2, $CHCl_3$). $^1$H-NMR: δ 2.89–3.15 (m, 5H), 3.71–3.73 (m, 3H), 3.82–3.83 (m, 3H), 4.46 (br d, J=5.5 Hz, 1H), 4.53 (d, J=5.7 Hz, 2H), 5.18–5.32 (m, 2H), 5.84–5.95 (m, 1H), 6.69 (d, J=8.0 Hz, 2H), 7.12 (t, J=8.0 Hz, 1H). $^{13}$C-NMR: δ, 22.60, 34.48, 42.13, 46.87, 52.03, 55.21, 65.54, 107.41, 117.69, 121.48, 122.20, 126.85, 132.73, 134.11, 155.65, 157.22, 173.62. HMRS for $C_{17}H_{21}O_5NNa$ (M+Na): calcd, 342.1317; found, 342.1305.

Synthesis of 1-N-allyloxycarbonyloxy-2-deoxystreptamine (11) as illustrated in FIG. 3:

11

Compound 11: A buffer was made by dissolving HEPES free acid (9.53 g, 40 mMol; Sigma company) and $CaCl_2$ (510 mg, 4 mMol counting the $H_2O$ content) in $H_2O$, adjusting the pH to 7.8 and diluting to a final volume of 100 ml. The final buffer was 400 mM in HEPES and 40 mM in $CaCl_3$. 2-Deoxystreptamine 10 (50 mg, 308 mMmol; supplied from Sandoz pharmaceutical company) was dissolved in the HEPES buffer (3 ml) and diluted with DMF (3 ml; dimethylformamide) to give a solution 200 mM in HEPES and 20 mM in $CaCl_2$. The reaction was then treated with diallyl carbonate (175 mg, 1.233 mmol) and subtilysin BPN' (10 mg). The reaction was allowed to proceed for 7 days with 3 more additions of the same amount of diallyl carbonate. The reaction was then filtered and the solvent was removed. The residue was loaded onto a column (1×20 cm) of Amberlite CG-50 anion exchange resin ($NH_4$ form) and eluted with a linear gradient of 0–3% $NH_3$ to afford 58 mg of 11 as the free base (76% yield). $[\alpha]_D$+5.9° (c:1, $H_2O$). $H^1$NMR ($CD_3OD$, Bruker AMX-500): δ 1.28 (ddd, $J_1=J_2=J_3$=12.5 Hz, 1H, H2 eq), δ 2.02 (ddd, $J_1$=12.5 Hz, $J_2=J_3$=4 Hz, 1H, H2ax), δ 2.69 (m, 1H, H3), δ 3.04 (dd, $J_1=J_2$=9 Hz 1H, H4), δ 3.20 (m, 2H, H5, H6), 3.46 (m, 1H, H1), 4.52 (m, 2H, allylic protons), 5.17 (dd, $J_1$=10.5 Hz, $J_2$=1.5 Hz, 1H, terminal vinyl trans proton), 5.30 (dd, $J_1$=17 Hz, $J_2$=1.5 Hz, 1H, terminal vinyl cis proton), 5.93 (m, 1H, internal vinyl proton); $^{13}C$ NMR ($CD_3OD$, Bruker AMX-500): δ 36.2, 52.3, 53.1, 66.4, 76.5, 78.0, 78.3, 117.4, 134.5, 158.6; HRMS for $C_{10}H_{18}N_2O_5$ (M+Na): calcd, 269.1113; found, 269.1105.

Synthesis of 1-N-Toluenesulfonamido-3-N-allyloxy-carbonyl-oxy-3,4,5-acetyloxy-2-deoxystreptamine (11a) product not shown in FIG. 3:

Compound 11a: Compound 11 (31 mg, 0.191 mmol) was dissolved in 3 ml of methanol and treated with triethylamine (38 mg, 0.373 mmol) followed by p-toluenesulfonyl chloride (60 mg, 0.315 mmol). The reaction was stirred under argon for 3 hours and the solvent was removed. The residue was treated with 2 ml each of pyridine and acetic anhydride. After an additional 3 hours, the solvent was removed and the residue picked up in EtOAc and washed with water, saturated bicarbonate solution and brine. The solution was then dried and rotary evaporated and purified on 5 g of silica gel using a gradient of 2%–3%–4% MeOH in $CHCl_3$ to afford 62 mg of product (49% yield). $H^1$ NMR ($CDCl_3$ Bruker AMX-500): δ 1.65 (ddd, $J_1=J_2=J_3$=12.5 Hz, 1H, H2 eq), 1.75 (s, 3H, acetate methyl), 1.97 (s, 3H, acetate methyl), 2.02 (s, 3H, acetate methyl), 2.33 (ddd, $J_1$=12.5 Hz, $J_2=J_3$= 4.5 Hz, 1H, H2ax), 2.43 (s, 3H, tosyl methyl), 3.47 (m, 1H, H3), 3.83 (m, 1H, H1), 4.53 (m, 2H, allylic protons), 4.90 (dd, $J_1=J_2$=10 Hz, 1H, H4), 4.95 (dd, $J_1=J_2$=10 Hz, 1H, H6), 5.07 (dd, $J_1=J_2$=10 Hz, 1H, H5), 5.15–5.3 (m, 3H, terminal vinyl protons and carbamate NH proton), 5.56 (d, J=8Hz, 1H, sulfonamide NH), 5.88 (m, 1H, internal vinyl proton), d 7.31 (d, J=2 Hz, 2H, tosyl aromatic protons proximal to the methyl), 7.74 (d, J=2 Hz, 2H, tosyl aromatic protons proximal to the sulfonamide); $^{13}C$ NMR ($CDCl_3$, Bruker AMX-500): δ 20.4, 20.4, 20.6, 21.4, 29.6, 35.4, 49.3, 52.1, 65.6, 71.8, 72.9, 73.1, 117.6, 126.8, 129.7, 132.6, 137.8, 143.4, 155.5, 169.5, 171.0; HRMS for $C_{23}H_{30}N_2O_{10}S$ (M+Cs): calcd, 659.0675; found, 659.0650.

Synthesis of N-allyloxycarbonyl-2-methylindoline (13) as illustrated in FIG. 4:

13

Compound 13: 130 mg (1.0 mmol) of 12 (Aldich chemical company) and 220 mg (1.5 mmol) of diallyl carbonate were mixed. 10 mL of phosphate buffer (0.1M, pH 8.0) and 50 mg of Subtilisin BPN' were added. The mixture was stirred at rt for 92 hours, then extracted (EtOAc) and concentrated in vacuo. The product was isolated by silicagel preparative TLC (EtOAc/Hex 1:20) to afford 13 mg (6%) of liquid 13. $[\alpha]_D$+51° (c: 0.2, $CHCl_3$). $^1$H-NMR: δ 1.31 (d, J=6.3 Hz, 3H), 2.64 (dd, J=1.8, 16.0 Hz, 1H), 3.37 (dd, J=9.6, 16.0 Hz, 1H), 4.53–4.65 (m, 1H), 4.75 (d, J=5.3 Hz, 2H), 5.27 (br d, J=10.5 Hz, 2H), 5.37 (br d, J=17.2 Hz, 1H), 5.94–6.10 (m, 1H), 6.97 (t, J=7.4 Hz, 1H), 7.00–7.22 (m, 2H), 7.74–7.80 (br s, 1H). $^{13}C$-NMR: δ 21.03, 35.71, 55.22, 65.78, 115.30, 117.73, 122.61, 124.91, 127.33, 129.90, 132.58, 141.23, 152.65. HMRS for $C_{13}H_{16}NO_2$ (M+H): calcd, 240.1000; found, 240.1009.

Synthesis of 1,2-dimethylindoline (14) as illustrated in FIG. 4:

14

Compound 14: A solution of 13 mg (0.06 mmol) of 13 in 3 mL of ether was added dropwise to a stirred suspension of 5 mg (0.13 mmol) of $LiAlH_4$ in 6 mL of ether at 0° C. After 2 hours stirring at 0° C., water and NaOH 1N were added and the mixture was extracted (EtOAc). The extract was washed with brine, dried with $Na_2SO_4$ and the solvent removed in vacuo. The product was isolated by silicagel flash chromatography (ether/Hexanes 1:10) to afford 8.2 mg (93%) of volatile liquid 12. $^1$H-NMR: δ 1.32 (d, J=6.1 Hz, 3H), 2.59 (dd, J=10.4, 15.3 Hz, 1H), 2.71 (s, 3H), 3.08 (dd, J=8.2, 15.3 Hz, 1H), 3.34–3.44 (m, 1H), 6.45 (d, J=7.8 Hz, 1H), 6.65 (t, J=7.3 Hz, 1H), 7.03–7.10 (m, 2H). $^{13}C$-NMR: δ 18.69, 33.66, 37.27, 62.74, 107.08, 117.71, 123.90, 127.25, 129.11, 153.43. HMRS for $C_9H_{10}N$ (M—$CH_3$): calcd, 132.0813; found, 132.0813.

Synthesis of N-acetyl-2-amino-1-phenylethanol acetate (17) as illustrated in FIG. 5 (reaction 1):

20% yield, 92% ee
40% yield, 87% ee

Compound 17: A mixture of 2-amino-1-phenylethanol 15 (50 mg; Aldrich chemical company), DMF (0.27 ml; dimethylformamide), vinyl acetate (0.18 ml), 0.1 M pH 7 phosphate buffer (0.009 ml), and subtilisin BPN' (10 mg) was stirred at 40° C. for 72 hrs. Conversion of the alcohol to acetate was 40% as estimated by the UV absorption of the acetate and the alcohol seen on the TLC plate. The enantiomeric excess of the acetate was determined to be 87% ee by HPLC analysis (CHIRALCEL OD-H, hexane/IPA 10/1, 1.1 ml/min). The acetamide-alcohol can be prepared in situ by mixing the aminoalcohol with vinyl acetate.
$^1$H-NMR (400 MHz, CDCl$_3$) δ 1.85 (s, 3H, CH$_3$), 2.01 (s, 3H, CH$_3$), 3.45, 3.59 (two m (8 lines), 2H, AB of ABXM, $J_{AX}$=8.4 Hz, $J_{AM}$=5.6 Hz, $J_{BX}$=4.3 Hz, $J_{BM}$=6.3 Hz, $J_{AB}$=14.0 Hz, —CH$_2$NHAc), 5.77 (dd, 1H, X of ABX, $J_{XA}$=8.4 Hz, $J_{XB}$=4.3 Hz, benzylic proton), 6.65 (br t, 1H, 3.9 Hz, —NH), 7.2–7.3 (m, 5H, phenylic protons); $^{13}$C-NMR (100 MHz, CDCl$_3$) δ 21.1, 22.9, 44.2, 74.5, 126.3, 128.3, 128.6, 137.9, 170.3, 170.6.; HRMS calcd for C$_{12}$H$_{15}$O$_3$N$_1$ 222.1130 (M+H$^+$), found 222.1128.

Synthesis of compound 18:

2g

Compound 18: A mixture of racemic amino alcohol 15 (Aldrich: 10 mg) is suspended in 0.10 Molar methylene chloride at 0° C. and exposed to triethylamine (1.1 equiv.) and acetic anhydride (1.0 equiv.) and allowed to stir at 25° C. for 12 hours under argon. The reaction is then quenched with water and subsequently followed by standard workup and column chromatography to afford the bisacetylated compound 18.

Hydrolysis of the Acetamide-acetate to Form Compounds 19 and 20 with >99% ee of Compound 20 as Illustrated in FIG. 5 (Reaction 2):

Compounds 19 and 20: A mixture of the acetate 18 (10 mg; prepared from 15, triethylamine (1.1 equiv.), acetic anhydride (1.0 equiv.) in 0.10 Molar methylene chloride at 0° C. for 1 hour, followed by standard workup and column chromatography), 0.1 M pH 7 phosphate buffer (0.2 ml), diisopropyl ether (0.2 ml) and lipase PS-800 (5 mg) was stirred at rt for 24 hrs. Hydrolysis of the acetate was 50% as estimated by the UV absorption of the acetate and the alcohol seen on the TLC plate. The enantiomeric excess of the acetate was determined to be >99% ee by HPLC analysis (CHIRALCEL OD-H, hexane/IPA 10/1, 1.1 ml/min).

Synthesis of Compound 22 as Illustrated in FIG. 5, Reaction 3:

50% yield
96% ee

Compound 22: A mixture of the 2-amino-1-phenylethanol 15 (50 mg; Aldrich chemical company), vinyl butyrate 32 (0.5 ml; Aldrich chemical), and lipase PS-30 (10 mg) was stirred at 40° C. for 72 hrs. Conversion of the alcohol to butyrate was 50% as estimated by the UV absorption of the butyrate and the alcohol seen on the TLC plate. The enantiomeric excess of the acetate was determined to be 96% ee by HPLC analysis (CHIRALCEL OD-H, hexane/IPA 10/1, 1.1 ml/min). The butyramide-alcohol 21 can be prepared in situ by mixing the aminoalcohol with vinyl butyrate.

Synthesis of N-Allyloxycarbonyl-2-amino-1-phenylethanol (23) as illustrated in FIG. 5, reaction 4:

30% yield
40% ee

Compound 23: Chemical method: 2-Amino-1-phenylethanol 15(0.50 g, 3.64 mmol) suspended in dry CH$_2$Cl$_2$ (20 mL) was treated with Et$_3$N (triethylamine) (0.53 mL, 3.80 mmol) and allylchloroformate (0.41 mL, 3.86 mmol) for 30 min. The mixture was diluted with CH$_2$Cl$_2$ and washed with 1N KHSO$_4$ and brine, dried (MgSO$_4$), filtered and concentrated in vacuo. Silica gel column chromatography (eluent: CH$_2$Cl$_2$/MeOH, 95/5, v/v) gave the desired product (742 mg) as a glass in 92% yield.

Enzymatic method (method A) (with purpose to get a high ee): 2-Amino-1-phenylethanol 15 (27 mg, 0.20 mmol) was suspended in 0.1 M phosphate buffer (1 mL) such that the pH of the mixture was 8.0. After addition of subtilisin BPN' (10 mg) and allylcarbonate (43 μL, 0.30 mmol) the mixture was stirred for 24 hours. Another portion of allylcarbonate (43 μL, 0.30 mmol) was added and stirring was continued for 48 hours. During this period the pH of mixture was kept around 7.5 by adding 0.1 M phosphate buffer of pH 10.5. The mixture was acidified with 1N KHSO$_4$ and extracted with EtOAc (ethylacetate). The combined organic layers were washed with brine, dried (MgSO$_4$), filtered and concentrated in vacuo. Silica gel column chromatography (eluent: CH$_2$Cl$_2$/MeOH, 95/5, v/v) gave the desired product (6 mg) as a glass in 15% yield. The e.e. was determined by HPLC (chiralcel OD-H) using hexanes/IPA, 95/5, v/v as eluent and found to be 40%.

Synthesis of compound 24 as illustrated in FIG. 5. reaction 4:

24

40% yield
>95% ee

Compound 24: To a solution of N-allyloxycarbonyl-2-amino-1-phenylethanol 23 (50 mg, 0.23 mmol) in vinylacetate (1 mL), CCL (40 mg) or PS-30 (40 mg) was added. After stirring for 7 days, the mixture was concentrated in vacuo. Silica gel column chromatography (eluent: hexanes/EtOAc, 4/1, with gradient to 3/1, v/v) gave the desired product (20 mg) as an oil in 35% yield. The e.e was determined by HPLC (chiralcel OD-H) using hexanes/iPrOH, 99/1, v/v as eluent and found to be >95%.

$R_f$ 0.29 (eluent: EtOAc/hexanes, 1/2, v/v); $^1$H NMR (400 MHz, CDCl$_3$) δ 2.10 (s, 3H, OAc), 3.51, 3.62 (m (7 lines), m (8 lines), 2H, AB of ABXM, $J_{AX}$=8.0 Hz, $J_{AM}$=6.1 Hz, $J_{BX}$=4.0 Hz, $J_{BM}$=6.9 Hz, $J_{AB}$=14.0 Hz, C$\underline{H}_2$NH), 4.55 (d, 2H, J=5.5 Hz, C$\underline{H}_2$O), 4.82–5.83 (dd, 1H, $J_{BX}$=4.0 Hz, $J_{BM}$=6.9 Hz, C$\underline{H}$OH), 5.02 (bt, 1H, NH), 5.21 (br d, 1H, $J_{bc}$=10.4 Hz, CH$_2$CH$_c$=CH$_a\underline{H}_b$), 5.29 (dq, 1H, $J_{ab}$=$J_{ad}$=1.2 Hz, $J_{ac}$=17.2 Hz, CH$_{2(d)}$CH$_c$=C$\underline{H}_a$H$_b$), 5.83 (dd, 1H, $J_{XA}$=8.0 Hz, $J_{XB}$=4.0 Hz, C$\underline{H}$OAc), 5.86–5.95 (m, 1H, CH$_2$C$\underline{H}_c$=CH$_2$), 7.28–7.38 (m, 5H, Ph); $^{13}$C NMR (100 MHz, CDCl$_3$) δ 21.05, 45.77, 65.63, 74.61, 117.73, 126.33, 128.36, 128.60, 132.68, 137.55, 156.05, 170.13; HRMS (EI; m/e) calcd for C$_{14}$H$_{17}$NO$_4$ (M+H$^+$) 264.1236, found 264.1231.

Synthesis of N-Allyloxycarbonyl-2-amino-1-phenylethanol acetate (26) as illustrated in FIG. 5. reaction 5:

26

40% yield
>95% ee

Compound 26: Chemical method: Racemic N-allyloxycarbonyl-2-amino-1-phenylethanol 25 (51 mg, 0.23 mmol; see chemical synthesis for 23) was dissolved in dry pyridine (0.5 mL) and treated with acetic anhydride (0.33 mL, mmol). After stirring for 4 hours. at rt, the mixture was concentrated to a small volume in vacuo, dissolved in EtOAc, washed with 1N KHSO$_4$ and brine, dried (MgSO$_4$), filtered and concentrated in vacuo. Silica gel column chromatography (eluent: hexanes/EtOAc, 4/1, with gradient to 3/1, v/v) gave the desired product (50 mg) as an oil in 83% yield.

Enzymatic method (lipase): To a solution of N-allyloxycarbonyl-2-amino-1-phenylethanol 25 (50 mg, 0.23 mmol) in vinylacetate (1 mL), CCL (40 mg) or PS-30 (40 mg) was added. After stirring for 7 days, the mixture was concentrated in vacuo. Silica gel column chromatography (eluent: hexanes/EtOAc, 4/1, with gradient to 3/1, v/v) gave the desired product (20 mg) as an oil in 35% yield. The e.e was determined by HPLC (chiralcel OD-H) using hexanes/iPrOH, 99/1, v/v as eluent and found to be >95%.

Enzymatic method (subtilisin BPN'): To N-allyloxycarbonyl-2-amino-1-phenylethanol (50 mg, 0.23 mmol) dissolved in DMF/water, 97/3, v/v (0.28 mL) vinylacetate (90 μL, 1.46 mmol)) and subtilisin BPN' (10 mg) was added. After stirring for 3 days, the mixture was concentrated in vacuo. Silica gel column chromatography (eluent: hexanes/EtOAc, 4/1, with gradient to 3/1, v/v) gave the desired product (16 mg) as an oil in 27% yield. The e.e was determined by HPLC (chiralcel OD-H) using hexanes/IPA, 99/1, v/v as eluent and found to be 18%.

$R_f$ 0.29 (eluent: EtOAc/hexanes, 1/2, v/v); $^1$H NMR (400 MHz, CDCl$_3$) δ 2.10 (s, 3H, OAc), 3.51, 3.62 (m (7 lines), m (8 lines), 2H, AB of ABXM, $J_{AX}$=8.0 Hz, $J_{AM}$=6.1 Hz, $J_{BX}$=4.0 Hz, $J_{BM}$=6.9 Hz, $J_{AB}$=14.0 Hz, C$\underline{H}_2$NH), 4.55 (d, 2H, J=5.5 Hz, C$\underline{H}_2$O), 4.82–5.83 (dd, 1H, $J_{BX}$=4.0 Hz, $J_{BM}$=6.9 Hz, C$\underline{H}$OH), 5.02 (bt, 1H, NH), 5.21 (br d, 1H, $J_{bc}$=10.4 Hz, CH$_2$CH$_c$=CH$_a\underline{H}_b$), 5.29 (dq, 1H, $J_{ab}$=$J_{ad}$=1.2 Hz, $J_{ac}$=17.2 Hz, CH$_{2(d)}$C$\underline{H}_a$C$_b$), 5.83 (dd, 1H, J=8.0 Hz, $J_{XB}$=4.0 Hz, C$\underline{H}$OAC), 5.86–5.95 (m, 1H, CH$_2$C$\underline{H}_c$=CH$_2$), 7.28–7.38 (m, 5H, Ph); $^{13}$C NMR (100 MHz, CDCl$_3$) δ 21.05, 45.77, 65.63, 74.61, 117.73, 126.33, 128.36, 128.60, 132.68, 137.55, 156.05, 170.13; HRMS (EI; m/e) calcd for C$_{14}$H$_{17}$NO$_4$ (M+H$^+$) 264.1236, found 264.1231.

Figure 6:
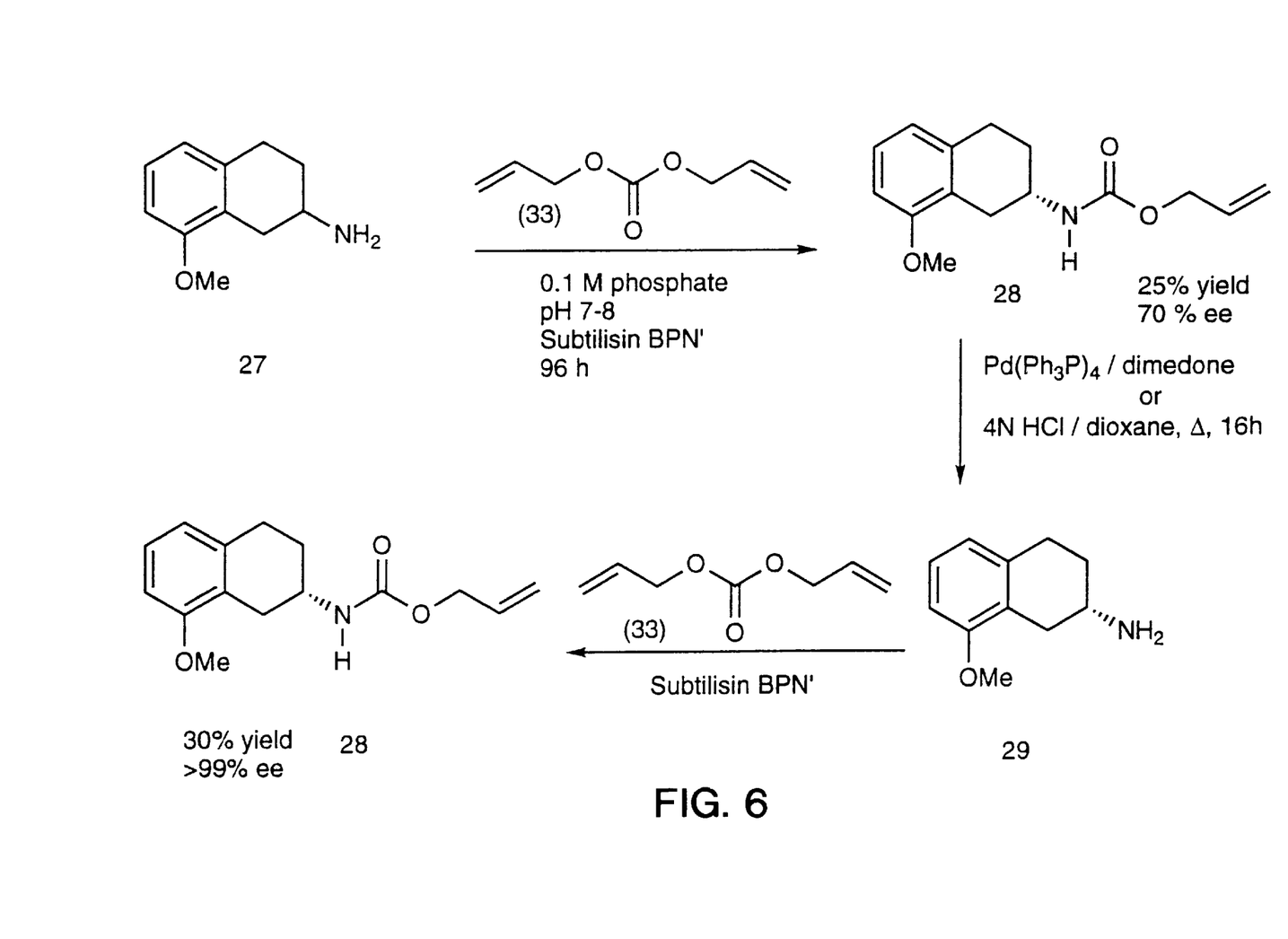
FIG. 6 illustrates a two step enzymatic resolution/protection of the secondary amine 27 with diallyl carbonate, aqueous buffer and subtilisin BPN'. The first resolution establishes a 70% ee which is followed by a deprotection and second resolution to obtain compound 28 in >99% enantiomeric excess (ee).

Synthesis of N-Allyloxy-2-amino-8-methoxy-tetrahydro-naphtalene (28) as illustrated in FIG. 6):

28

Compound 28: Chemical method: 2-Amino-8-methoxy-tetrahydronaphtalene (52.5 mg, 0.30 mmol; available from Sandoz pharmaceutical or Aldrich chemical company) suspended in dry CH$_2$Cl$_2$ (2 mL) was treated with Et$_3$N (43 μL, 0.31 mmol) and allylchloroformate (33 μL, 0.31 mmol) for 2 hours. The mixture was diluted with CH$_2$Cl$_2$ and washed with iN KHSO$_4$ and brine, dried (MgSO$_4$), filtered and concentrated in vacuo. Silica gel column chromatography (eluent: EtOAc/hexanes, 1/4, v/v) gave the desired product (43 mg) as a solid in 55% yield.

Enzymatic method: 2-Amino-8-methoxy-tetrahydronaphtalene (14 mg, 0.08 mmol) was suspended in 0.1 M phosphate buffer (1 mL) such that the pH of the mixture was 8.0. After addition of subtilisin BPN' (6 mg) and allylcarbonate (18 μL, 0.13 mmol) the mixture was stirred for 24 hours. Another portion of allylcarbonate (18 μL, 0.13 mmol) was added and stirring was continued for 48 hours. During this period the pH of mixture was kept around 7.5 by adding 0.1 M phosphatebuffer of pH 10.5. The mixture was acidified with iN KHSO$_4$ and extracted with EtOAc. The combined organic layers were washed with brine, dried (MgSO$_4$), filtered and concentrated in vacuo. Silica gel column chromatography (eluent: CH$_2$Cl$_2$/MeOH, 95/5, v/v) gave the desired product (5 mg) as a solid in 25% yield. The e.e was determined by HPLC (chiralcel OD-H) using hexanes/IPA, 95/5, v/v as eluent and found to be 70% (S).

The same procedure was used, starting from 2-amino-8-methoxy-tetrahydronaphtalene 29—vida infra (70% ee, S) to give the product in >99% ee (yield 30%).

$R_f$ 0.50 (eluent: EtOAc/hexanes, 1/2, v/v); $^1$H NMR (400 MHz, CDCl$_3$) δ 1.69–1.79 (m, 1H, cH), 2.01–2.08 (m, 1H, cH), 2.45, 3.09 (two dd, 2H, AB of ABX, $J_{AX}$=8.1 Hz, $J_{BX}$=5.5 Hz, $J_{AB}$=17.2 Hz, CH$_2$ cH), 2.80–2.93 (m, 2H, cH), 3.80 (s, 3H, OMe), 3.98–4.03 (m, 1H, C$\underline{H}$NH), 4.80 (d, 1H, NH), 4.57 (d, 2H, J=5.2 Hz, C$\underline{H}_2$O), 5.21 (dq, 1H, $J_{ba}$=$J_{bd}$=0.8 Hz, $J_{bc}$=10.4 Hz, CH$_2$CH$_c$=CH$_a\underline{H}_b$), 5.31 (dq, 1H, $J_{ab}$=$J_{ad}$=1.0 Hz, $J_{ac}$=17.2 Hz, CH$_2$CH$_c$=C$\underline{H}_a$H$_b$), 5.88–5.97 (m, 1H, CH$_2$C$\underline{H}_c$=CH$_2$), 6.66 (d, 1H, J=7.9 Hz, Ar), 6.72 (d, 1H, J=7.9 Hz, Ar), 7.11 (t, 1H, J=7.9 Hz, Ar); $^{13}$C NMR (100 MHz, CDCl$_3$) δ 27.25, 28.51, 229.95, 46.63, 55.19, 65.36, 106.95, 117.62, 120.88, 126.43, 136.80, 140.47, 157.41; HRMS (EI; m/e) calcd for C$_{15}$H$_{19}$NO$_3$ (M+H$^+$) 262.1443, found 262.1440.

Synthesis of intermediate compound 2-amino-8-methoxy-tetrahydronaphtalene 29 as illustrated in FIG. 6:

29

Compound 29: N-Allyloxycarbonyl-2-amino-8-methoxy-tetrahydro-naphtalene 28 (50 mg, 0.19 mmol) was deprotected according to the method of Boullanger et al. *Tetrahedron letters* 1986 27, 2599 (using Pd(OAc)$_2$ (2.2 mg, 0.01 mmol), Et$_3$N (4.3 μL, 0.031 mmol), Et$_3$SiH (triethylsilane) (47 μL, 0.29 mmol; commercially available from Aldrich) in CH$_2$Cl$_2$ (0.8 mL) employing a reaction time of 2 days. The amine 29 was isolated in 70% yield (23 mg).

What is claimed is:

1. A method for enantioselectively carbamating one enantiomer of a racemic primary or secondary amine for producing a chiral carbamate, the method comprising, the step of enantioselectively carbamating the racemic amine using a homocarbonate as a carbamating agent and a hydrolase as a carbamating catalyst for producing the chiral carbamate, the hydrolase being of a type employable with the homocarbonate for enantioselectively carbamating the racemic amine, wherein the homocarbonate is selected from a group consisting of dimethyl carbonate, diethyl carbonate, and diallyl carbonate;

wherein the racemic amine is selected from the group consisting of primary and secondary amines;

with the proviso that if the racemic amine has a ring nitrogen then the ring nitrogen cannot have an α-substitution.

2. The method for enantioselectively carbamating one enantiomer of a racemic amine for producing a chiral carbamate as described in claim 1 wherein the racemic amine is selected from the group consisting of aziridine, α-aminoalcohol, β-aminoester, and diaminocyclitol.

3. A method for separating a first enantiomer of a primary or secondary amine from a second enantiomer of the amine, the method comprising the following steps:

Step A: enzymatically carbamating the first enantiomer of the amine using a homocarbonate as an carbamating agent and a hydrolase as a carbamating catalyst to form a chiral carbamate, the hydrolase being of a type employable with the homocarbonate for enantioselectively carbamating the racemic amine, with the proviso that if the racemic amine has a ring nitrogen then the ring nitrogen cannot have an α-substitution; then Step B: Separating the chiral carbamate of said Step A from the second enantiomer of the amine; and then Step C: Decarbamating the chiral carbamate of said Step B to obtain the first enantiomer of the amine, separate from the second enantiomer of the amine.

4. The method for separating a first enantiomer of an amine from a second enantiomer of the amine as described in claim 3, wherein:

in said Step A: the homocarbonate is selected from the group consisting of dimethyl carbonate, diethyl carbonate, and diallyl carbonate.

5. The method for separating a first enantiomer of an amine from a second enantiomer of the amine as described in claim 3, wherein:

in said Step A: the hydrolase is selected from the group consisting of *Pseudomonas cepacia* (PS-30), *Pseudomonas cepacia* (PS-800), and *Candida cylindracea* lipase.

6. The method for separating a first enantiomer of an amine from a second enantiomer of the amine as described in claim 3, wherein:

in said Step B: the chiral carbamate of said Step A is separated chromatographically from the second enantiomer of the amine.

7. The method for separating a first enantiomer of an amine from a second enantiomer of the amine as described in claim 3, wherein:

in said Step C: the chiral carbamate is decarbamated by hydrolysis.

8. The method for separating a first enantiomer of an amine from a second enantiomer of the amine as described in claim 3, wherein the amine is selected from the group consisting of aziridine, α-aminoalcohol, β-aminoester, and diaminocyclitol.

9. A method for enantioselectively alkylating one enantiomer of a racemic primary or secondary amine, the method comprising the following steps:

Step A: Enzymatically carbamating an enantiomer of the racemic amine using a homocarbonate as a carbamating agent and a hydrolase as a carbamating catalyst for producing a chiral carbamate, the hydrolase being of a type employable with the homocarbonate for enantioselectively carbamating the racemic amine, with the proviso that if the racemic amine has a ring nitrogen then the ring nitrogen cannot have an α-substitution; then Step B: Separating the chiral carbamate of said Step A from unreacted amine; and then Step C: reducing the chiral carbamate of said Step B to obtain a chiral N-alkyl amine.

10. The method for enantioselectively alkylating one enantiomer of a racemic amine as described in claim 9, wherein:

in said Step C: the chiral carbamate is reduced with LiAlH$_4$.

11. The method for enantioselectively alkylating one enantiomer of a racemic amine as described in claim 9, wherein:

in said Step A: the homocarbonate is selected from the group consisting of dimethyl carbonate, diethyl carbonate, and diallyl carbonate.

12. The method for enantioselectively alkylating one enantiomer of a racemic amine as described in claim 9, wherein:

in said Step A: the hydrolase is selected from the group consisting of of *Pseudomonas cepacia* (PS-30),

*Pseudomonas cepacia* (PS-800), and *Candida cylindracea* lipase.

13. The method for enantioselectively alkylating one enantiomer of a racemic amine as described in claim 9, wherein:
   in said Step B: the chiral carbamate of said Step A is separated chromatographically from unreacted amine.

14. The method for enantioselectively alkylating one enantiomer of a racemic amine as described in claim 9, wherein the racemic amine is selected from the group consisting of aziridine, α-aminoalcohol, β-aminoester, and diaminocyclitol.

15. An improved method for carbamating a primary or secondary racemic amamine using a homocarbonate as a carbamating agent and a hydrolase as a carbamating catalyst for producing a carbamate, wherein the improvement comprises the following steps:
   Step A: Enantioselectively carbamating one enantiomer of a racemic mixture of the amine, the hydrolase being of a type employable with the homocarbonate for producing a mixture including a chiral carbamate and an unreacted enantiomer of the amine; and then
   Step B: resolving said mixture of the unreacted enantiomer of the amine and the chiral carbamate for producing an enantiomerically pure chiral carbamate.

16. An improved method for carbamating a primary or secondary racemic amine using a homocarbonate as a carbamating agent and a hydrolase as a carbamating catalyst for producing a carbamate, wherein the improvement comprises the following steps:
   Step A: Enantioselectively carbamating one enantiomer of a racemic mixture of the amine, the hydrolase being of a type employable with the homocarbonate for producing a mixture including a chiral carbamate and an unreacted enantiomer of the amine; and then
   Step B: reducing the chiral carbamate obtained in said Step B to obtain a chiral N-methyl amine.

17. An improved method as described in claim 16 comprising the following additional step after said Step A and prior to said Step B:
   Step C: separating the chiral carbamate obtained in said Step A from unreacted amine.

18. A method for enantioselectively carbamating one enantiomer of a mixture of enantiomers of primary or secondary amines comprising:
   enantioselectively carbamating the mixture of amines with diallylcarbonate using a hydrolase as catalyst to produce an enantioselected carbamate and an enantioselected amine.

19. The method for enantioselectively carbamating one enantiomer of a mixture of enantiomers of primary or secondary amines as described in claim 18 wherein the hydrolase is selected from a group consisting of serine-type esterases, subtilisin, and lipase from *C. cylindracea*.

20. A method for enantioselectively carbomating one enantiomer of a mixture of enantiomers of primary or secondary amines as described in claim 18 wherein the primary or secondary amines are selected from a group consisting of aziridines, α-aminoalcohols, β-aminoesters, and diaminocyclitols.

21. A method for enantioselectively carbomating one enantiomer of a mixture of enantiomers of primary or secondary amines as described in claim 18 further comprising the following steps following said enantioselectively carbamating step:
   separating the enantioselected carbamate from the enantioselected amine; and then
   decarbamating the enantioselected carbamate for producing an enantioselected amine.

22. A method for enantioselectively carbamating one enantiomer of a mixture of enantiomers of primary or secondary amines as described in claim 18 further comprising the following steps following said enantioseletively carbamating step:
   separating the enantioseleted carbamate from the enantioselected amine; and then
   reducing the enantioselected carbamate to produce enantioselected alkylated amine.

23. A method for enantioselectively carbamating one enantiomer of a mixture of enantiomers of amines selected from the group consisting essentially of aziridine or diaminocyclitol comprising:
   enantioselectively carbamating the amine with a homocarbonate selected from the group consisting of dimethylcarbonate, diethylcarbonate, or diallylcarbonate using a serine-type esterase or protease to produce an enantioselected carbamate and an enantioselected amine.

* * * * *